(12) United States Patent
Uriu

(10) Patent No.: US 9,695,459 B2
(45) Date of Patent: *Jul. 4, 2017

(54) METHOD FOR DETERMINING WHETHER OR NOT TEST SAMPLE CONTAINS PHYTOPATHOGENIC OOMYCETE

(71) Applicant: Panasonic Intellectual Property Management Co., Ltd., Osaka (JP)

(72) Inventor: Yoshitsugu Uriu, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/948,282

(22) Filed: Nov. 21, 2015

(65) Prior Publication Data

US 2017/0037444 A1 Feb. 9, 2017

(30) Foreign Application Priority Data

Aug. 3, 2015 (JP) ................................. 2015-153028
Aug. 6, 2015 (JP) ................................. 2015-155734

(51) Int. Cl.
| | | |
|---|---|---|
| *C12N 1/04* | (2006.01) | |
| *C12Q 1/04* | (2006.01) | |
| *C12N 1/14* | (2006.01) | |
| *C12N 3/00* | (2006.01) | |

(52) U.S. Cl.
CPC ................. *C12Q 1/04* (2013.01); *C12N 1/14* (2013.01); *C12N 3/00* (2013.01)

(58) Field of Classification Search
None
See application file for complete search history.

(56) References Cited

U.S. PATENT DOCUMENTS

| 9,410,210 B2 * | 8/2016 | Mach ....................... C12Q 1/24 |
| 2007/0231852 A1 * | 10/2007 | Oppedahl ................ C12N 1/14 435/34 |
| 2013/0071356 A1 * | 3/2013 | Galiana ................... C12R 1/645 424/93.5 |

FOREIGN PATENT DOCUMENTS

| JP | 2005-287337 | * 10/2005 | ............... C12Q 1/06 |
| WO | WO 2011156258 A1 * 12/2011 | ............... C12Q 1/24 |

OTHER PUBLICATIONS

Takahashi, Reiko et al. Development and application of a loop-mediated isothermal amplification assay for rapid detection of Pythium helicoides. FEMS Microbiol Lett 355 (2014) 28-35.*
Paul F. Morris et. al. "Chemotropic and Contact Responses of Phytophthora sojae Hyphae to Soybean Isoflavonods and Artificial Substrates", Plant Physiol. (1998) vol. 117: pp. 1171-1178.
Tadaoki Inaba et. al. "Morphology of Hyphae in Leaf Tissues Infected with Java Corn Downy Mildew Fungus, Peronosclerospora maydis, in Relation to Sporulation Ability", Ann. Phytopath. Soc. Japan 46: 200-208 (1980).

* cited by examiner

*Primary Examiner* — Scott Long
*Assistant Examiner* — Nghi Nguyen
(74) *Attorney, Agent, or Firm* — McDermott Will & Emery LLP

(57) ABSTRACT

The present invention provides a method for determining whether or not a test sample contains a phytopathogenic oomycete selectively from two kinds of oomycetes of a phytopathogenic oomycete and a non-phytopathogenic oomycete. The method according to the present invention comprises: (a) putting the test sample on a front surface of a cellulose film; wherein the cellulose film has a thickness of not less than 0.5 micrometers and not more than 3.7 micrometers; (b) leaving the test sample at rest for not less than 4 hours and not more than 8 hours after the step (a); (c) observing a back surface of the film after the step (b); and (d) determining that the test sample contains the phytopathogenic oomycete, if an oomycete is found on the back surface of the film in the step (c).

15 Claims, 9 Drawing Sheets

METHOD FOR DETERMINING WHETHER OR NOT TEST SAMPLE CONTAINS PHYTOPATHOGENIC OOMYCETE

BACKGROUND

1. Technical Field

The present invention relates to a method for determining whether or not a test sample contains a phytopathogenic oomycete.

2. Description of the Related Art

Japanese Patent Application laid-open Publication No. 2005-287337A discloses a method for counting the number of mold cells in a specimen by the culture for a short time and capable of accurately counting the cell number. FIG. 12 shows a cross-sectional view of a microporous membrane supporting material used for the method disclosed therein. According to this method, the extended multiple pseudomycelia of a mold cell 13 cultured by a liquid culture or a mold cell 13 cultured on a microporous membrane 1 of a microporous membrane supporting material 4 are photographed and the shape, area and luminous intensity are recognized and analyzed by an image analytic means 10. The number of the mold cells 13 can be counted by the culture for a short time. The microporous membrane 1 is interposed between a pressing ring 2 and a base 3.

SUMMARY

The present invention provides a method for determining whether or not a test sample contains a phytopathogenic oomycete, the method comprising:

(a) putting the test sample on a front surface of a cellulose film;

wherein the cellulose film has a thickness of not less than 0.5 micrometers and not more than 3.7 micrometers;

(b) leaving the test sample at rest for not less than 4 hours and not more than 8 hours after the step (a);

(c) observing a back surface of the film after the step (b); and (d) determining that the test sample contains the phytopathogenic oomycete, if an oomycete is found on the back surface of the film in the step (c).

The present invention provides a method for determining whether or not a test sample contains a phytopathogenic oomycete selectively from two kinds of oomycetes of a phytopathogenic oomycete and a non-phytopathogenic oomycete.

DETAILED DESCRIPTION OF THE EMBODIMENT

First, an oomycete will be described. Oomycetes are roughly divided into a phytopathogenic oomycete and a non-phytopathogenic oomycete. An example of the phytopathogenic oomycete is *Pythium helicoides, Pythium myriotylum, Phytophthora nicotianae*, or *Pythium aphanidermatum*. These phytopathogenic oomycetes cause *pythium* red blight and a root rot disease. First, these phytopathogenic oomycetes infect a root of a plant. Then, these phytopathogenic oomycetes cause the root of the plant to rot. Finally, these phytopathogenic oomycetes kill the plant. An example of the non-phytopathogenic oomycete is *Pythium catenulatum, Pythium torulosum* or *Pythium inflatum*.

The term "phytopathogenic" means to have pathogenicity to plants. The term "non-phytopathogenic" means not to have pathogenicity to plants. Even if an oomycete has pathogenicity, however, if the oomycete has no pathogenicity to plants, the oomycete is non-phytopathogenic. In other words, if an oomycete does not have adverse effects on plants, the oomycete is non-phytopathogenic. The prefix "non-" included in the term "non-phytopathogenic" does not modify "phyto". The prefix "non-" modifies "pathogenic".

Hereinafter, the embodiment of the present invention will be described in more detail with reference to the drawings.

(Step (a))

In the step (a), a test sample is put on a front surface of a cellulose film having a thickness of not less than 0.5 micrometers and not more than 3.7 micrometers. The importance of the thickness of the cellulose film will be described later.

Figure 1:
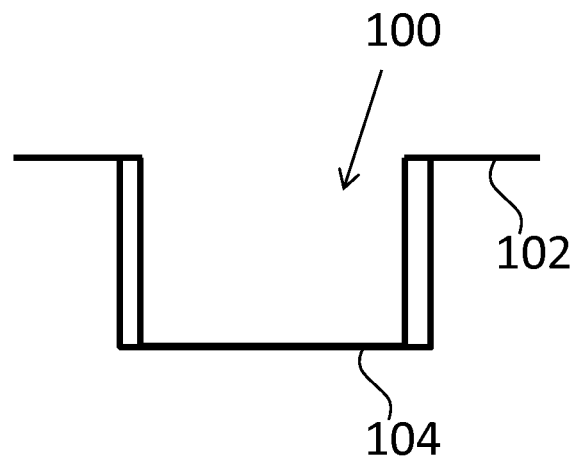
FIG. 1 shows a cross-sectional view of a first container 100.

In particular, as shown in FIG. 1, a container 100 is prepared. It is desirable that the container 100 comprises a flange 102 at the upper end thereof. The bottom surface of the container 100 is formed of a cellulose film 104. It is desirable that the cellulose film 104 is supported by a substrate (not shown in FIG. 1). This will be described later.

Figure 3:
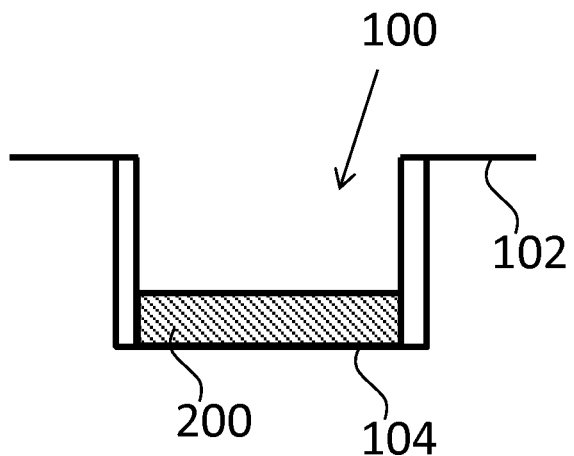
FIG. 3 shows a cross-sectional view of the first container 100 to which a test sample has been supplied.
Figure 4:
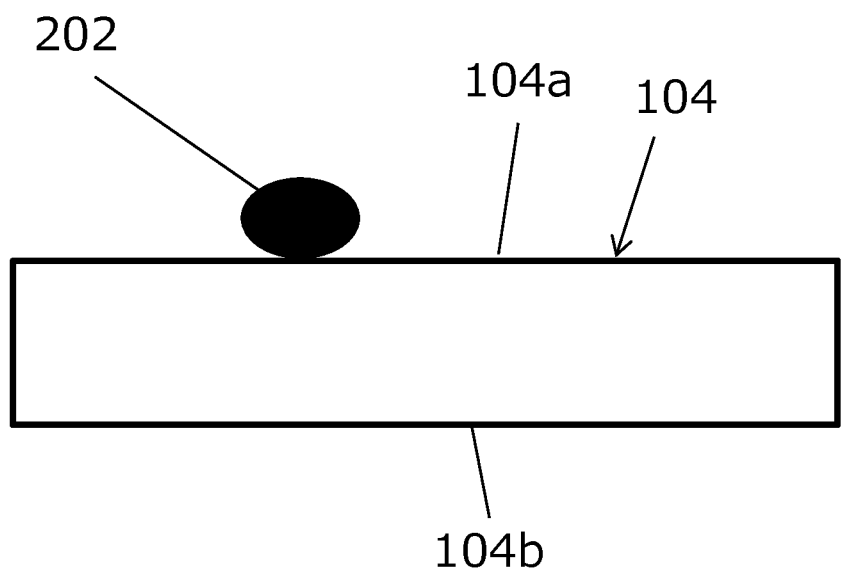
FIG. 4 shows a cross-sectional view of the cellulose film 104 having a front surface on which a phytopathogenic oomycete has been put.

As shown in FIG. 3, a test sample 200 is supplied to the inside of this container 100. In this way, the test sample 200 is put on the front surface 104a of the cellulose film 104. When the test sample 200 contains a phytopathogenic oomycete 202, the phytopathogenic oomycete 202 is put on the front surface 104a of the cellulose film 104, as shown in FIG. 4.

The test sample 200 is solid, liquid, or gaseous. It is desirable that the test sample 200 is solid or liquid. An example of the solid test sample 200 is soil or a crushed plant. Another example is an agricultural material such as vermiculite, rock wool or urethane. An example of the liquid test sample 200 is agricultural water, a solution used for hydroponic culture, a liquid used for washing a plant, a liquid extracted from a plant, a liquid used for washing an agricultural material, or a liquid used for washing clothing or shoes of a worker.

(Step (b))

In the step (b), the test sample 200 is left at rest for a certain incubation time after the step (a). The incubation time is not less than 4 hours and not more than 8 hours. Hereinafter, the importance of the thickness of the cellulose film 104 and the incubation time will be described.

Figure 5:
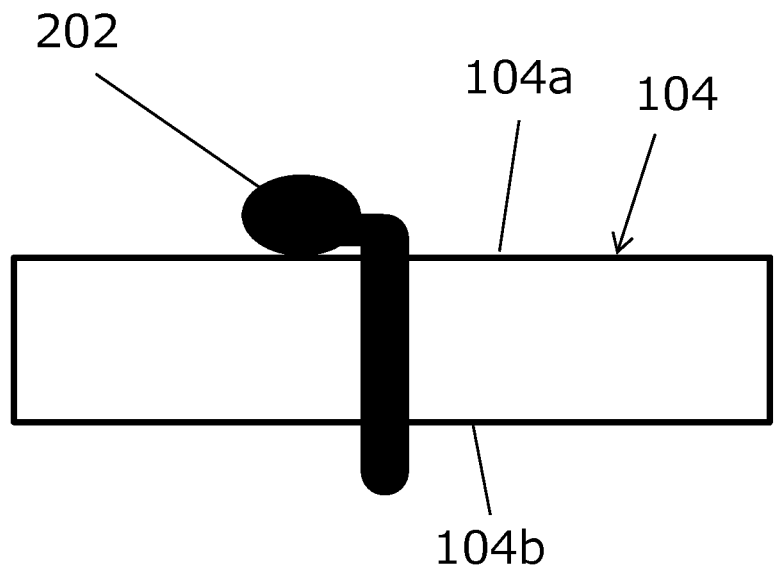
FIG. 5 is a cross-sectional view showing a state where the phytopathogenic oomycete has penetrated the cellulose film 104.

In the step (b), various oomycetes contained in the test sample 200 are grown. As demonstrated in the experiments which will be described later, if both of the following requirements (I) and (II) are satisfied, the phytopathogenic oomycete 202 grows up so as to penetrate the cellulose film 104, as shown in FIG. 5. As a result, the phytopathogenic oomycete 202 appears on a back surface 104b of the cellulose film 104.

Requirement (I): The cellulose film 104 has a thickness of not less than 0.5 micrometers and not more than 3.7 micrometers.

Requirement (II): The incubation time is not less than 4 hours and not more than 8 hours.

If both of the above requirements (I) and (II) are satisfied, the non-phytopathogenic oomycete seldom penetrate the cellulose film 104. For this reason, the non-phytopathogenic oomycete seldom appears on the back surface 104b of the cellulose film 104. In this way, the phytopathogenic oomycete 202 appears on the back surface 104b selectively. In other words, the phytopathogenic oomycete 202 appears outside of the container 100 selectively.

In case where the cellulose film 104 has a thickness of more than 3.7 micrometers, neither the non-phytopathogenic oomycete nor the phytopathogenic oomycete penetrates the cellulose film 104 within the incubation time of 4-8 hours. Therefore, in case where the cellulose film 104 has a thickness of more than 3.7 micrometers, the selectivity is lost. When the cellulose film 104 has a thickness of less than 0.5 micrometers, not only the phytopathogenic oomycete but also the non-phytopathogenic oomycete penetrates the cellulose film 104 within the incubation time of 4-8 hours. Therefore, the selectivity is lost when the cellulose film 104 has a thickness of less than 0.5 micrometers.

In case where the incubation time is less than 4 hours, a sufficient number of the phytopathogenic oomycetes 202 fail to penetrate the cellulose film 104. In case where the incubation time is more than 12 hours, not only the phytopathogenic oomycete but also the non-phytopathogenic oomycete penetrates the cellulose film 104. In the present invention, the incubation time is not less than 4 hours and not more than 8 hours.

Figure 2:
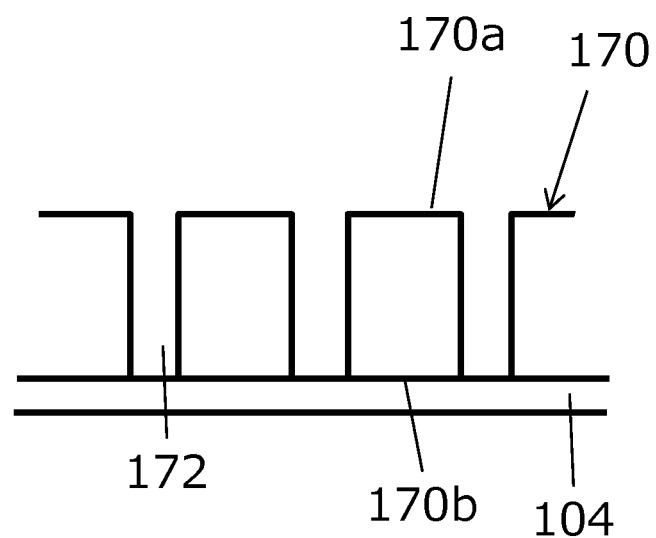
FIG. 2 shows a cross-sectional view of a cellulose film 104 supported by a back surface of a substrate 170.

As shown in FIG. 2, the cellulose film 104 may comprise a substrate 170 comprising a through hole 172 on at least one of the front surface 170a and the back surface 170b thereof. In FIG. 2, the cellulose film 104 comprises the substrate 170 on the front surface thereof. In other words, in FIG. 2, the substrate 170 comprises the cellulose film 104 on a back surface 170b thereof. It is desirable that the through hole 172 has a diameter of more than 5 micrometers. More desirably, the through hole 172 has a diameter of not less than 8 micrometers. In case where the through hole 172 has a diameter of not more than 5 micrometers, the non-phytopathogenic oomycete seldom reaches the inside of the through hole 172. As a result, the non-phytopathogenic oomycete fails to be brought into contact with the front surface of the cellulose film 104. For more detail, see Japanese Patent Applications No. 2015-111885 and No. 2015-111886, both of which were filed on Jun. 2, 2015.

Needless to say, as long as the cellulose film 104 is stretched taut, the substrate 170 is not required. In other words, if it is difficult to stretch the cellulose film 104 taut, the substrate 170 for supporting the cellulose film 104 is used.

The reference number 170a indicates the front surface of the substrate 170. As shown in FIG. 2, it is desirable that the substrate 170 has a plurality of through holes 172. The thickness of the substrate 170 is not limited; however, as one example, it is desirable that the substrate 170 has a thickness of not less than 1 micrometer and not more than 500 micrometers. The cellulose film 104 is significantly thin. However, if the cellulose film 104 is arranged on the substrate 170, it is easy to handle the cellulose film 104.

A culture medium may be supplied to the test sample 200 to accelerate the incubation of the oomycete. In particular, a culture medium may be supplied to the inside of the container 100 containing the test sample 200. It is desirable that the culture medium is liquid. The culture medium may be supplied in the step (b). Alternatively, the culture medium may be supplied prior to the step (b). In other words, the culture medium may be supplied in the step (a). The culture medium may be supplied to the inside of the container 100 prior to the step (a).

Figure 6:
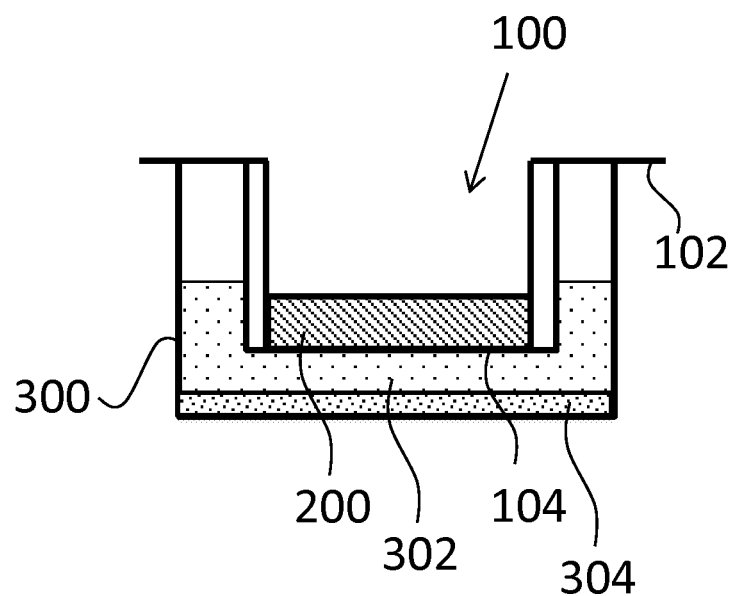
FIG. 6 shows a cross-sectional view of one example of a method for accelerating the incubation of the oomycete.

FIG. 6 shows another method for accelerating the incubation of the oomycete. As shown in FIG. 6, it is desirable that the back surface 104b of the cellulose film 104 is in contact with a liquid culture medium 302. First, a second container 300 having the liquid culture medium 302 therein is prepared. Hereinafter, the container 100 is referred to as "first container 100" to distinguish it from the second container 300. The first container 100 is stacked on the second container 300 in such a manner that the lower surface of the flange 102 is in contact with the upper end of the second container 300. In other words, the first container 100 is supported by the upper end of the second container 300. In this way, the liquid culture medium 302 is sandwiched between the back surface 104b of the cellulose film 104 and the bottom surface of the second container 300.

Alternatively, after the first container 100 is stacked on the second container 300, the liquid culture medium 302 may be supplied between the back surface 104b of the cellulose film 104 and the bottom surface of the second container 300.

In place of the liquid culture medium 302, a viscous solid culture medium may also be used. As shown in FIG. 6, both of a solid culture medium 304 and the liquid culture medium 302 may be used. In this case, the liquid culture medium 302 is sandwiched between the solid culture medium 304 and the cellulose film 104. As shown in FIG. 5, the incubation of the phytopathogenic oomycete 202 which has appeared on the back surface 104b is accelerated by at least one of the liquid culture medium 302 and the solid culture medium 304.

(Step (c))

In the step (c), the back surface 104b of the cellulose film 104 is observed after the step (b). It is desirable that the back surface 104b is observed using an optical microscope.

The phytopathogenic oomycete 202 appears on the back surface 104b of the cellulose film 104, as described in the step (b). On the other hand, the non-phytopathogenic oomycete does not appear on the back surface 104b of the cellulose film 104. In this way, in the present invention, the phytopathogenic oomycete 202 appears on the back surface 104b of the cellulose film 104 selectively.

In other words, the phytopathogenic oomycete 202 penetrates the cellulose film 104, whereas the non-phytopathogenic oomycete does not penetrate the cellulose film 104. For this reason, the non-phytopathogenic oomycete does not appear on the back surface 104b of the cellulose film 104. In this way, the phytopathogenic oomycete 202 appears on the back surface 104b selectively. In other words, the phytopathogenic oomycete 202 appears outside of the first container 100 selectively.

In the step (c), it is observed whether or not the phytopathogenic oomycete 202 appears on the back surface 104b of the cellulose film 104.

In particular, whether or not the phytopathogenic oomycete 202 appears on the back surface 104b of the cellulose film 104 is observed as below.

Figure 8:
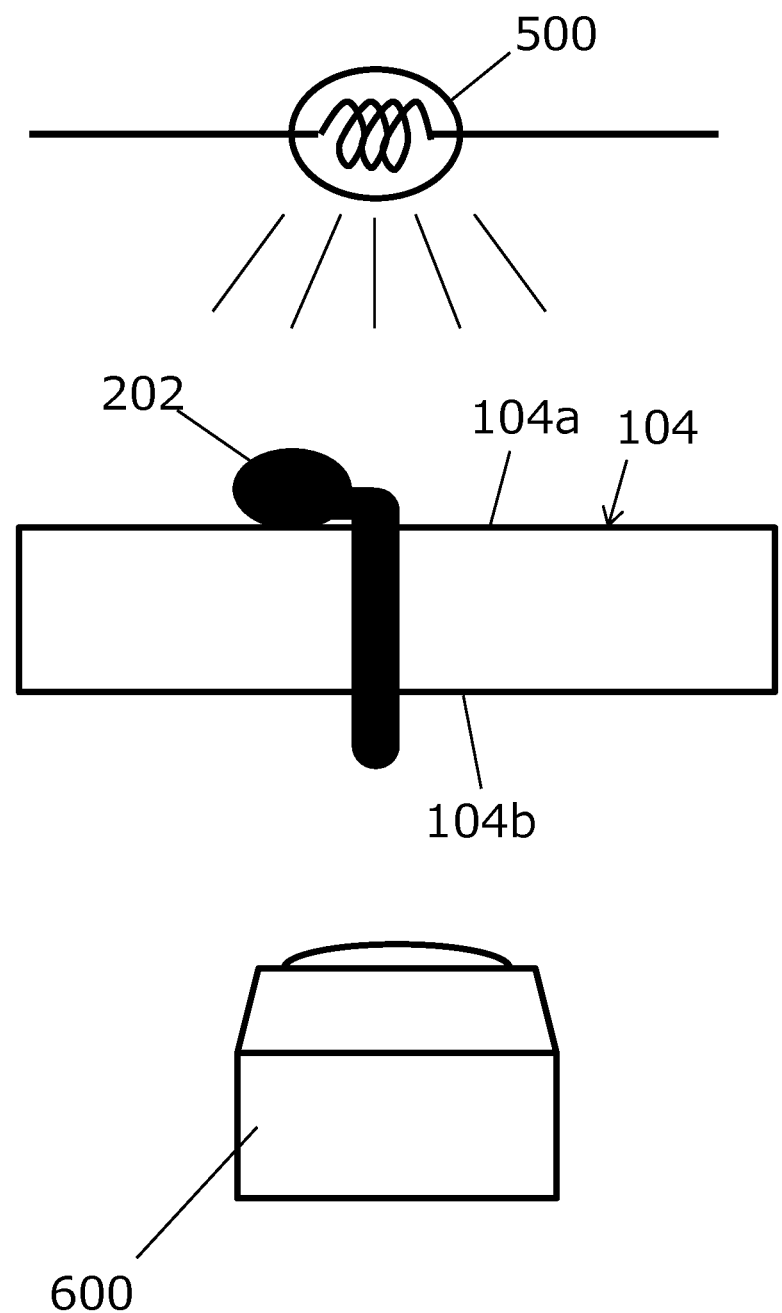
FIG. 8 is a cross-sectional view showing how to observe the oomycete from the back surface of the cellulose film 104.

As shown in FIG. 8, while the cellulose film 104 is irradiated with light emitted from a light source 500 arranged above the front surface 104a of the cellulose film 104, the phytopathogenic oomycete 202 is observed optically using a microscope 600 arranged below the back surface 104b of the cellulose film 104.

Figure 7:
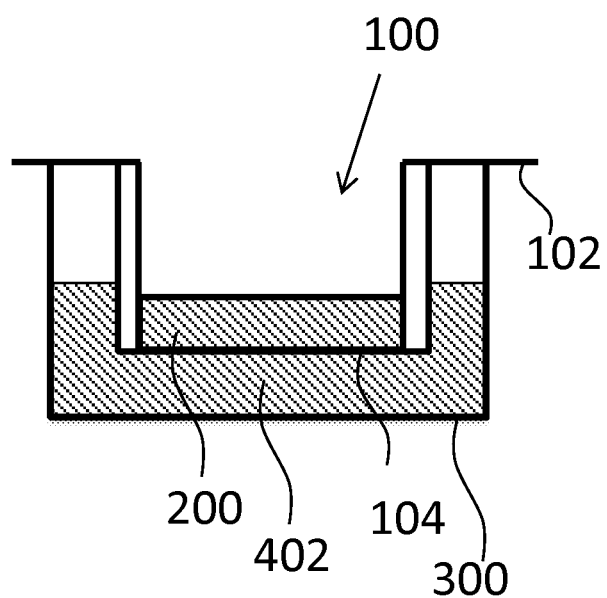
FIG. 7 shows a cross-sectional view, subsequently to FIG. 6, of one example of a method for accelerating the incubation of the oomycete.

The liquid culture medium 302 and the solid culture medium 304 are removed from the second container 300. Then, a fluorescent agent having oomycete combining ability is added to the inside of the second container 300. Hereinafter, such a fluorescent agent is referred to as "oomycete fluorescent agent". The reference number of the oomycete fluorescent agent is 402. Then, as shown in FIG. 7, the first container 100 is stacked on the second container 300 having the oomycete fluorescent agent 402 therein. Alternatively, the oomycete fluorescent agent 402 may be supplied between the back surface 104b of the cellulose film 104 and the bottom surface of the second container 300 after the first container 100 is stacked on the second container 300.

A part of the phytopathogenic oomycete 202 which has appeared on the back surface 104b of the cellulose film 104 is dyed with the oomycete fluorescent agent 402. Since the first container 100 is separated from the second container 300 by the cellulose film 104, the oomycete fluorescent agent 402 does not spread into the first container 100. For this reason, the non-phytopathogenic oomycete contained in the first container 100 is not dyed with the oomycete fluorescent agent 402.

Figure 9:
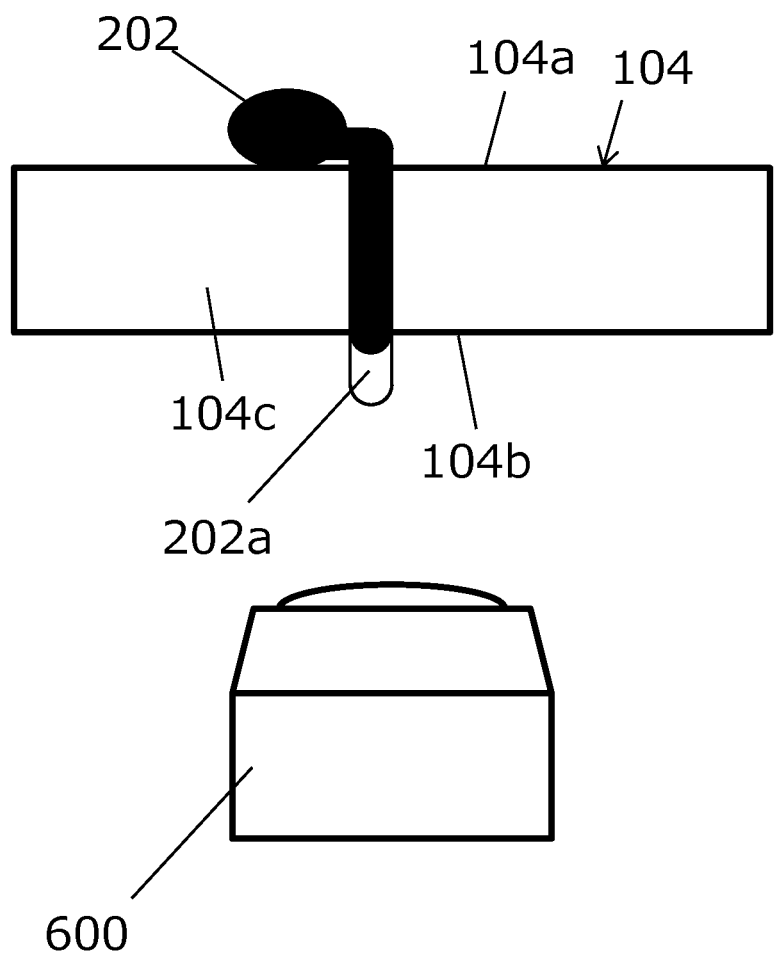
FIG. 9 is a cross-sectional view showing how to observe the oomycete from the back surface of the cellulose film 104.
Figure 10:
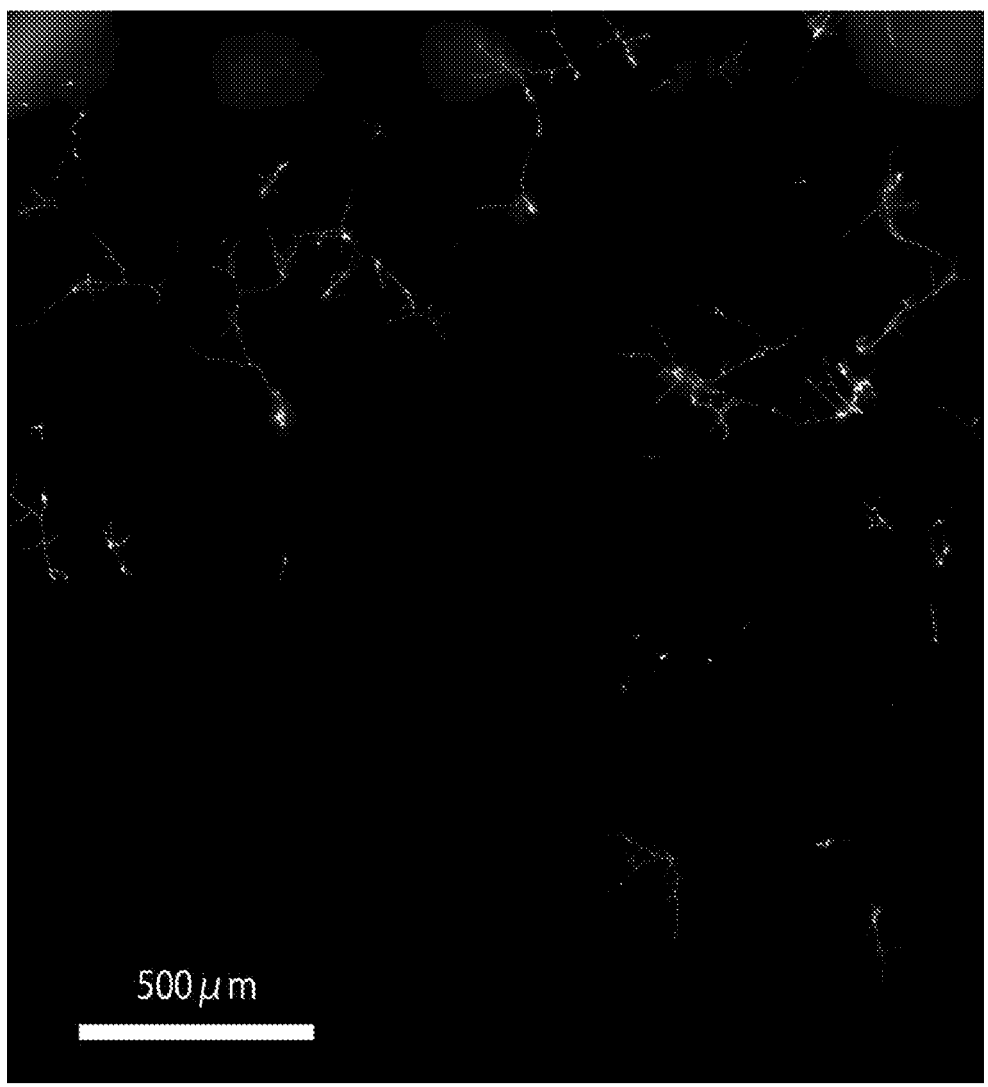
FIG. 10 is a microscope photograph of the back surface of the cellulose film 104 in the inventive example 1A.
Figure 11:
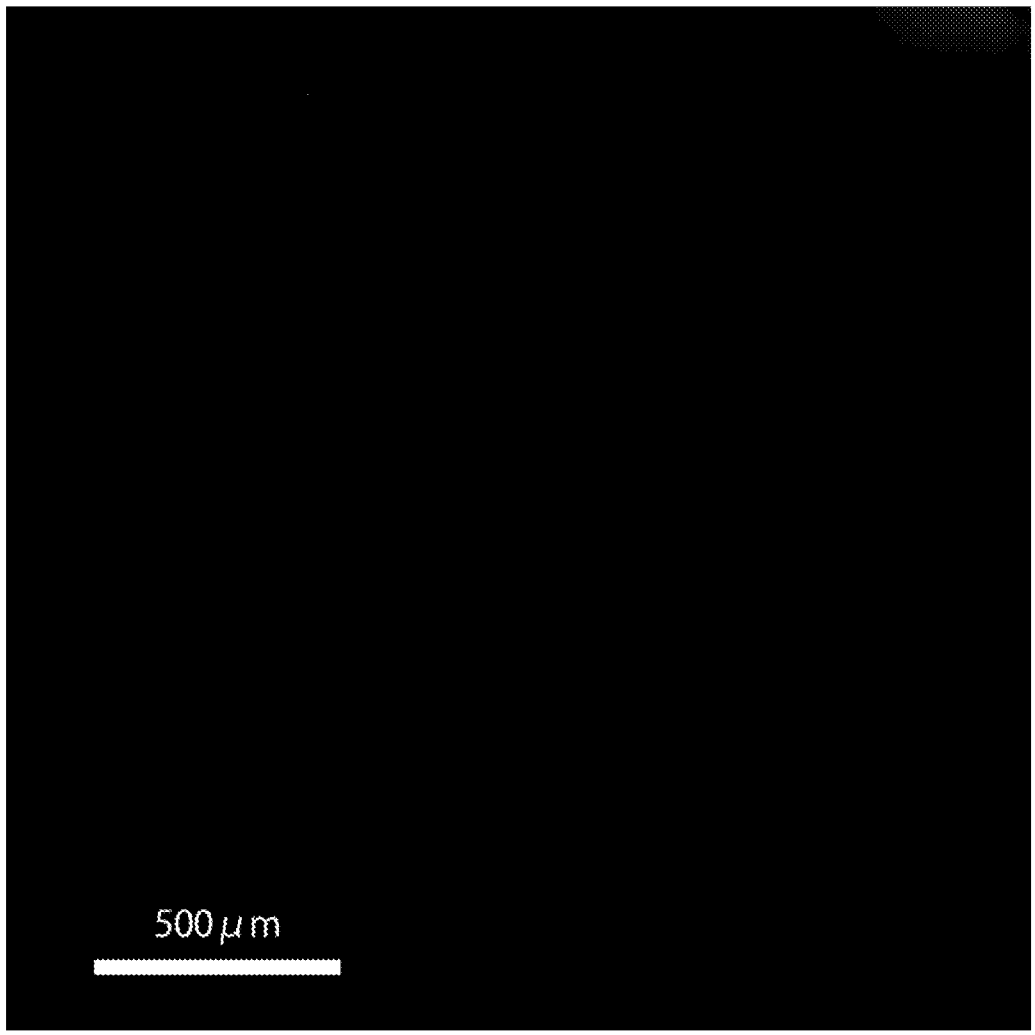
FIG. 11 is a microscope photograph of the back surface of the cellulose film 104 in the comparative example 2A.
Figure 12:
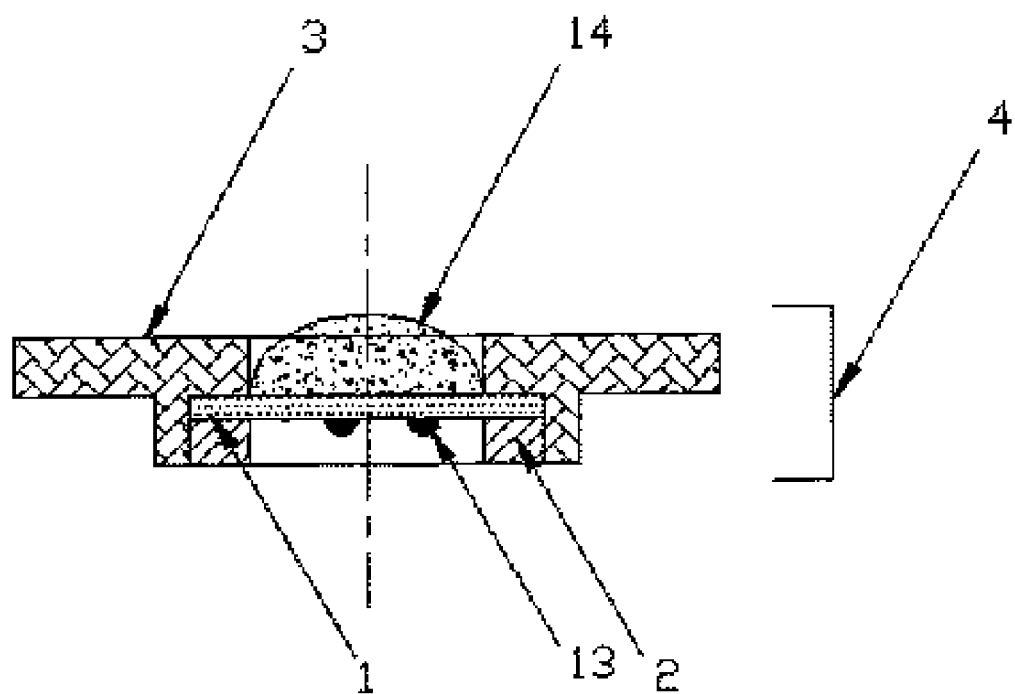
FIG. 12 shows a cross-sectional view of the microporous membrane supporting material used for the method for counting the number of mold cells disclosed in Japanese Patent Application laid-open Publication No. 2005-287337A.

As shown in FIG. 9, the phytopathogenic oomycete 202 dyed with the oomycete fluorescent agent 402 is observed using the epifluorescence microscope 600 located under the back surface 104b of the cellulose film 104. Needless to say, the phytopathogenic oomycete 202 may be observed without using the oomycete fluorescent agent 402.

(Step (d))

In the step (d), it is determined that the test sample contains a phytopathogenic oomycete, if an oomycete is found on the back surface 104b of the cellulose film 104 in the step (c). Needless to say, it is determined that the test sample does not contain a phytopathogenic oomycete, if an oomycete is not found on the back surface 104b of the cellulose film 104 in the step (c).

EXAMPLES

The present invention will be described in more detail with reference to the following examples.

(Incubation of *Pythium aphanidermatum*)

*Pythium aphanidermatum*, one of phytopathogenic oomycetes, was inoculated on a cornmeal agar culture medium together with dried turfgrass. Then, the culture medium was left at rest at a temperature of 25 degrees Celsius for 24 hours. *Pythium aphanidermatum* was given by Professor Kageyama, who belongs to Gifu University River Basin Research Center. The dried turfgrass was provided by drying Korean lawn grass sterilized in accordance with a high temperature and high pressure sterilization method at 60 degrees Celsius for approximately 24 hours.

Then, the dried turfgrass to which a pseudomycelium was adhered was picked up from the culture medium. The thus-picked dried turfgrass was provided afloat to the pure water contained in a petri dish. The volume of the pure water was 20 milliliters.

After 18 hours, the water contained in the petri dish was observed using an optical microscope. As a result, the present inventors confirmed that zoospores of *Pythium aphanidermatum* were released in the water contained in the petri dish. In this way, an aqueous solution containing *Pythium aphanidermatum* was provided. Hereinafter, this aqueous solution is referred to as "phytopathogenic aqueous solution".

(Preparation of Culture Medium)

A potato dextrose culture medium having a volume of 650 microliters was added as the liquid culture medium 302 to the second container 300. In this way, the second container 300 containing the liquid culture medium 302 was prepared.

Experiment 1

The experiment 1 is composed of inventive examples 1A-1C, a reference example 1D, a comparative example 1E, inventive examples 1F-1G, reference examples 1H-1I, and comparative examples 1J-1K.

Inventive Example 1A

The first container 100 shown in FIG. 1 was prepared as below.

First, cellulose (available from SIGMA-ALDRICH Co. LLC, trade name: Avicel PH-101) was dissolved in an ionic liquid to prepare a cellulose solution having a concentration of 2%. The ionic liquid was 1-butyl-3-methyl imidazolium chloride (available from SIGMA-ALDRICH Co. LLC).

The cellulose solution was warmed to 60 degrees Celsius. Then, the cellulose solution was applied by a spin coat method for thirty seconds at a rotation speed of 2,000 rpm onto a back surface of a container having a polyethylene terephthalate film on the bottom surface thereof (available from Merck KGaA, trade name: Millicell PIEP 12R 48). The polyethylene terephthalate film served as the substrate 170. The polyethylene terephthalate film randomly had a plurality of through holes 172 each having a diameter of eight micrometers. In this way, the cellulose film 104 having a thickness of 2.0 micrometers was formed on the back surface of the polyethylene terephthalate film.

The container was left at rest in ethanol at room temperature for 12 hours. In this way, 1-butyl-3-methyl imidazolium chloride was replaced with ethanol. In other words, 1-butyl-3-methyl imidazolium chloride was removed from the cellulose film 104.

Finally, the container was dried in a vacuum desiccator. In this way, the first container 100 shown in FIG. 1 was obtained. In FIG. 1, note that the polyethylene terephthalate film serving as the substrate 170 is not illustrated.

Then, as shown in FIG. 6, the first container 100 was stacked on the second container 300. The back surface 104b of the cellulose film 104 was in contact with the liquid culture medium 302. Subsequently, water having a volume of 200 microliters was added to the inside of the first container 100. Furthermore, the phytopathogenic aqueous solution containing 200 zoospores of *Pythium aphanidermatum* was added to the inside of the first container 100.

The first container 100 was left at rest at a temperature of 25 degrees Celsius for 6 hours. In other words, in the inventive example 1A, the incubation time was 6 hours.

An oomycete fluorescent agent (available from Becton Dickinson and Company, trade name: Calcofluor White (BD261195)) having a volume of 600 microliters was added to the inside of the second container 300. The final concentration of the fluorescent agent having oomycete combining ability was 0.005%.

Then, the back surface 104*b* of the cellulose film 104 was in contact with the fluorescent agent having oomycete combining ability. The first container 100 was left at rest at 25 degrees Celsius for 10 minutes. Since the first container 100 was separated from the second container 300 by the cellulose film 104, the fluorescent agent having oomycete combining ability did not spread into the first container 100.

Subsequently, the first container 100 was separated from the second container 300. The fluorescent agent having oomycete combining ability contained in the second container 300 was removed. Then, a buffer solution was added to the inside of the second container 300. The following Table 1 shows components contained in this buffer solution and their concentrations.

TABLE 1

| Component | Concentration (mmol/L) |
|---|---|
| NaCl | 137 |
| KCl | 2.7 |
| $Na_2HPO_4$ | 10 |
| $KH_2PO_4$ | 1.76 |

As shown in FIG. 9, the back surface 104*b* of the cellulose film 104 was observed using a fluorescent microscope 600 (available from Molecular Devices Japan K.K. Trade name: ImageXpress MICRO). Table 2 shows filters and a lens used for the fluorescent microscope 600.

TABLE 2

| | |
|---|---|
| Excitation filter | Band pass filter having a center wavelength of 377 nanometers and a band width of 11 nanometers |
| Fluorescence filter | Band pass filter having a center wavelength of 447 nanometers and a band width of 60 nanometers |
| Object lens | Magnification: 10 times/Numerical aperture: 0.30 |

FIG. 10 is a microscope photograph of the back surface 104*b* of the cellulose film 104 in the inventive example 1A. As seen in FIG. 10, pseudohyphae of *Pythium aphanidermatum* appear on the back surface 104*b*. This means that the pseudohyphae of *Pythium aphanidermatum* penetrated the cellulose film 104.

The number of the pseudohyphae of *Pythium aphanidermatum* which appeared on the back surface 104*b* was counted visually. The inventive example 1A was repeated two times-three times. As a result, the mean value of the number of the pseudohyphae of *Pythium aphanidermatum* which appeared on the back surface 104*b* was 54.0.

Inventive Example 1B

In the inventive example 1B, an experiment similar to the inventive example 1A was conducted, except that the cellulose solution had a concentration of 3% and that the cellulose film 104 had a thickness of 3.7 micrometers.

Inventive Example 1C

In the inventive example 1C, an experiment similar to the inventive example 1A was conducted, except that the cellulose solution had a concentration of 1% and that the cellulose film 104 had a thickness of 0.5 micrometers.

Reference Example 1D

An experiment similar to the inventive example 1A was conducted, except that the cellulose solution had a concentration of 0.5% and that the cellulose film 104 had a thickness of 0.2 micrometers.

Comparative Example 1E

In the comparative example 1E, an experiment similar to the inventive example 1A was conducted, except that the cellulose solution had a concentration of 5% and that the cellulose film 104 had a thickness of 12.4 micrometers.

Inventive Example 1F

In the inventive example 1F, an experiment similar to the inventive example 1A was conducted, except that the incubation time was 4 hours.

Inventive Example 1G

In the inventive example 1G, an experiment similar to the inventive example 1A was conducted, except that the incubation time was 8 hours.

Reference Example 1H

In the reference example 1H, an experiment similar to the inventive example 1A was conducted, except that the incubation time was 10 hours.

Reference Example 1I

In the reference example 1I, an experiment similar to the inventive example 1A was conducted, except that the incubation time was 12 hours.

Comparative Example 1J

In the comparative example 1J, an experiment similar to the inventive example 1A was conducted, except that the incubation time was 2 hours.

Comparative Example 1K

In the comparative example 1K, an experiment similar to the inventive example 1A was conducted, except that the incubation time was 24 hours.

Experiment 2

In the experiment 2, a non-phytopathogenic aqueous solution containing zoospores of *Pythium catenulatum* was used in place of the phytopathogenic aqueous solution containing zoospores of *Pythium aphanidermatum*. Unlike *Pythium aphanidermatum, Pythium catenulatum* is one kind of non-phytopathogenic oomycete. A non-phytopathogenic aqueous solution containing zoospores of *Pythium catenulatum* was prepared similarly to the case of the phytopathogenic aqueous solution containing zoospores of *Pythium aphanidermatum*. The experiment 2 is composed of comparative examples 2A-2K.

Comparative Example 2A

In the comparative example 2A, an experiment similar to the inventive example 1A was conducted, except that the non-phytopathogenic aqueous solution containing zoospores of *Pythium catenulatum* was used in place of the phytopathogenic aqueous solution containing zoospores of *Pythium aphanidermatum.*

FIG. 11 is a microscope photograph of the back surface 104*b* of the cellulose film 104 in the comparative example 2A. As seen in FIG. 11, pseudohyphae of *Pythium catenulatum* seldom appear on the back surface 104*b*. This means that the pseudohyphae of *Pythium catenulatum* did not penetrate the cellulose film 104.

Comparative Example 2B

In the comparative example 2B, an experiment similar to the comparative example 2A was conducted, except that the cellulose solution had a concentration of 3% and that the cellulose film 104 had a thickness of 3.7 micrometers.

Comparative Example 2C

In the comparative example 2C, an experiment similar to the comparative example 2A was conducted, except that the cellulose solution had a concentration of 1% and that the cellulose film 104 had a thickness of 0.5 micrometers.

Comparative Example 2D

In the comparative example 2D, an experiment similar to the comparative example 2A was conducted, except that the cellulose solution had a concentration of 0.5% and that the cellulose film 104 had a thickness of 0.2 micrometers.

Comparative Example 2E

In the comparative example 2E, an experiment similar to the comparative example 2A was conducted, except that the cellulose solution had a concentration of 5% and that the cellulose film 104 had a thickness of 12.4 micrometers.

Comparative Example 2F

In the comparative example 2F, an experiment similar to the comparative example 2A was conducted, except that the incubation time was 4 hours.

Comparative Example 2G

In the comparative example 2G, an experiment similar to the comparative example 2A was conducted, except that the incubation time was 8 hours.

Comparative Example 2H

In the comparative example 2H, an experiment similar to the comparative example 2A was conducted, except that the incubation time was 10 hours.

Comparative Example 2I

In the comparative example 2I, an experiment similar to the comparative example 2A was conducted, except that the incubation time was 12 hours.

Comparative Example 2J

In the comparative example 2J, an experiment similar to the comparative example 2A was conducted, except that the incubation time was 2 hours.

Comparative Example 2K

In the comparative example 2K, an experiment similar to the comparative example 2A was conducted, except that the incubation time was 24 hours.

Experiment 3

In the experiment 3, a phytopathogenic aqueous solution containing zoospores of *Pythium helicoides* was used in place of the phytopathogenic aqueous solution containing zoospores of *Pythium aphanidermatum*. Similarly to *Pythium aphanidermatum, Pythium helicoides* is also one kind of phytopathogenic oomycete. A phytopathogenic aqueous solution containing zoospores of *Pythium helicoides* was prepared similarly to the case of the phytopathogenic aqueous solution containing zoospores of *Pythium aphanidermatum*. The experiment 3 is composed of inventive examples 3A, 3F, and 3G, reference examples 3H and 3I, and comparative examples 3J and 3K.

Inventive Example 3A

In the inventive example 3A, an experiment similar to the inventive example 1A was conducted, except that the phytopathogenic aqueous solution containing zoospores of *Pythium helicoides* was used in place of the phytopathogenic aqueous solution containing zoospores of *Pythium aphanidermatum.*

Inventive Example 3F

In the inventive example 3F, an experiment similar to the inventive example 3A was conducted, except that the incubation time was 4 hours.

Inventive Example 3G

In the inventive example 3G, an experiment similar to the inventive example 3A was conducted, except that the incubation time was 8 hours.

Reference Example 3H

In the reference example 3H, an experiment similar to the inventive example 3A was conducted, except that the incubation time was 10 hours.

Reference Example 3I

In the reference example 3I, an experiment similar to the inventive example 3A was conducted, except that the incubation time was 12 hours.

Comparative Example 3J

In the comparative example 3J, an experiment similar to the inventive example 3A was conducted, except that the incubation time was 2 hours.

Comparative Example 3K

In the comparative example 3K, an experiment similar to the inventive example 3A was conducted, except that the incubation time was 24 hours.

Experiment 4

In the experiment 4, a phytopathogenic aqueous solution containing zoospores of *Pythium myriotylum* was used in place of the phytopathogenic aqueous solution containing zoospores of *Pythium aphanidermatum*. Similarly to *Pythium aphanidermatum*, *Pythium myriotylum* is also one kind of phytopathogenic oomycete. A phytopathogenic aqueous solution containing zoospores of *Pythium myriotylum* was prepared similarly to the case of the phytopathogenic aqueous solution containing zoospores of *Pythium aphanidermatum*. The experiment 4 is composed of inventive examples 4A, 4F, and 4G, reference examples 4H and 4I, and comparative examples 4J and 4K.

Inventive Example 4A

In the inventive example 4A, an experiment similar to the inventive example 1A was conducted, except that the phytopathogenic aqueous solution containing zoospores of *Pythium myriotylum* was used in place of the phytopathogenic aqueous solution containing zoospores of *Pythium aphanidermatum*.

Inventive Example 4F

In the inventive example 4F, an experiment similar to the inventive example 4A was conducted, except that the incubation time was 4 hours.

Inventive Example 4G

In the inventive example 4G, an experiment similar to the inventive example 4A was conducted, except that the incubation time was 8 hours.

Reference Example 4H

In the reference example 4H, an experiment similar to the inventive example 4A was conducted, except that the incubation time was 10 hours.

Reference Example 4I

In the reference example 4I, an experiment similar to the inventive example 4A was conducted, except that the incubation time was 12 hours.

Comparative Example 4J

In the comparative example 4J, an experiment similar to the inventive example 4A was conducted, except that the incubation time was 2 hours.

Comparative Example 4K

In the comparative example 4K, an experiment similar to the inventive example 4A was conducted, except that the incubation time was 24 hours.

Experiment 5

In the experiment 5, a phytopathogenic aqueous solution containing zoospores of *Pythium nicotianae* was used in place of the phytopathogenic aqueous solution containing zoospores of *Pythium aphanidermatum*. Similarly to *Pythium aphanidermatum*, *Pythium nicotianae* is also one kind of phytopathogenic oomycete. A phytopathogenic aqueous solution containing zoospores of *Pythium nicotianae* was prepared similarly to the case of the phytopathogenic aqueous solution containing zoospores of *Pythium aphanidermatum*. The experiment 5 is composed of inventive examples 5A, 5F, and 5G, reference examples 5H and 5I, and comparative examples 5J and 5K.

Inventive Example 5A

In the inventive example 5A, an experiment similar to the inventive example 1A was conducted, except that the phytopathogenic aqueous solution containing zoospores of *Pythium nicotianae* was used in place of the phytopathogenic aqueous solution containing zoospores of *Pythium aphanidermatum*.

Inventive Example 5F

In the inventive example 5F, an experiment similar to the inventive example 5A was conducted, except that the incubation time was 4 hours.

Inventive Example 5G

In the inventive example 5G, an experiment similar to the inventive example 5A was conducted, except that the incubation time was 8 hours.

Reference Example 5H

In the reference example 5H, an experiment similar to the inventive example 5A was conducted, except that the incubation time was 10 hours.

Reference Example 5I

In the reference example 5I, an experiment similar to the inventive example 5A was conducted, except that the incubation time was 12 hours.

Comparative Example 5J

In the comparative example 5J, an experiment similar to the inventive example 5A was conducted, except that the incubation time was 2 hours.

Comparative Example 5K

In the comparative example 5K, an experiment similar to the inventive example 5A was conducted, except that the incubation time was 24 hours.

Experiment 6

In the experiment 6, a non-phytopathogenic aqueous solution containing zoospores of *Pythium torulosum* was used in place of the phytopathogenic aqueous solution containing zoospores of *Pythium aphanidermatum*. Unlike *Pythium aphanidermatum*, *Pythium torulosum* is one kind of non-phytopathogenic oomycete. A non-phytopathogenic aqueous solution containing zoospores of *Pythium torulosum* was prepared similarly to the case of the phytopathogenic aqueous solution containing zoospores of *Pythium aphanidermatum*. The experiment 6 is composed of comparative examples 6A and 6F-6K.

Comparative Example 6A

In the comparative example 6A, an experiment similar to the inventive example 1A was conducted, except that the non-phytopathogenic aqueous solution containing zoospores of *Pythium torulosum* was used in place of the phytopathogenic aqueous solution containing zoospores of *Pythium aphanidermatum*.

Comparative Example 6F

In the comparative example 6F, an experiment similar to the comparative example 6A was conducted, except that the incubation time was 4 hours.

Comparative Example 6G

In the comparative example 6G, an experiment similar to the comparative example 6A was conducted, except that the incubation time was 8 hours.

Comparative Example 6H

In the comparative example 6H, an experiment similar to the comparative example 6A was conducted, except that the incubation time was 10 hours.

Comparative Example 6I

In the comparative example 6I, an experiment similar to the comparative example 6A was conducted, except that the incubation time was 12 hours.

Comparative Example 6J

In the comparative example 6J, an experiment similar to the comparative example 6A was conducted, except that the incubation time was 2 hours.

Comparative Example 6K

In the comparative example 6K, an experiment similar to the comparative example 6A was conducted, except that the incubation time was 24 hours.

Experiment 7

In the experiment 7, a non-phytopathogenic aqueous solution containing zoospores of *Pythium inflatum* was used in place of the phytopathogenic aqueous solution containing zoospores of *Pythium aphanidermatum*. Unlike *Pythium aphanidermatum*, *Pythium inflatum* is one kind of non-phytopathogenic oomycete. A non-phytopathogenic aqueous solution containing zoospores of *Pythium inflatum* was prepared similarly to the case of the phytopathogenic aqueous solution containing zoospores of *Pythium aphanidermatum*. The experiment 7 is composed of comparative examples 7A and 7F-7K.

Comparative Example 7A

In the comparative example 7A, an experiment similar to the inventive example 1A was conducted, except that the non-phytopathogenic aqueous solution containing zoospores of *Pythium inflatum* was used in place of the phytopathogenic aqueous solution containing zoospores of *Pythium aphanidermatum*.

Comparative Example 7F

In the comparative example 7F, an experiment similar to the comparative example 7A was conducted, except that the incubation time was 4 hours.

Comparative Example 7G

In the comparative example 7G, an experiment similar to the comparative example 7A was conducted, except that the incubation time was 8 hours.

Comparative Example 7H

In the comparative example 7H, an experiment similar to the comparative example 7A was conducted, except that the incubation time was 10 hours.

Comparative Example 7I

In the comparative example 7I, an experiment similar to the comparative example 7A was conducted, except that the incubation time was 12 hours.

Comparative Example 7J

In the comparative example 7J, an experiment similar to the comparative example 7A was conducted, except that the incubation time was 2 hours.

Comparative Example 7K

In the comparative example 7K, an experiment similar to the comparative example 7A was conducted, except that the incubation time was 24 hours.

The following Table 3-Table 5 show the number of the pseudohyphae which penetrated the cellulose film 104 in the experiments.

TABLE 3

| C.: Comparative I.: Inventive R.: Reference | Film thickness (μm) | Incubation time (hour) | Name of oomycete | Number of pseudohyphae which penetrated cellulose film 104 |
|---|---|---|---|---|
| C. example 1E | 12.4 | 6 | Pythium aphanidermatum (phytopathogenic) | 0 |
| I. example 1B | 3.7 | | | 25 |
| I. example 1A | 2.0 | | | 54.0 |
| I. example 1C | 0.5 | | | 80 |
| R. example 1D | 0.2 | | | 159.7 |
| C. example 2E | 12.4 | | Pythium catenulatum (non-phytopathogenic) | 0 |
| C. example 2B | 3.7 | | | 0 |
| C. example 2A | 2.0 | | | 0.3 |
| C. example 2C | 0.5 | | | 1.7 |
| C. example 2D | 0.2 | | | 11.0 |

TABLE 4

| C.: Comparative<br>I.: Inventive<br>R.: Reference | Film thickness (μm) | Incubation time (time) | Name of oomycete | Number of pseudohyphae which penetrated cellulose film 104 |
|---|---|---|---|---|
| C. example 1J | 2.0 | 2 | Pythium aphanidermatum (phytopathogenic) | 0.0 |
| I. example 1F | | 4 | | 7.7 |
| I. example 1A | | 6 | | 54.0 |
| I. example 1G | | 8 | | 100.3 |
| R. example 1H | | 10 | | 164.3 |
| R. example 1I | | 12 | | 189.3 |
| C. example 1K | | 24 | | Uncountable |
| C. example 3J | 2.0 | 2 | Pythium helicoides (phytopathogenic) | 0.0 |
| I. example 3F | | 4 | | 28.0 |
| I. example 3A | | 6 | | 51.5 |
| I. example 3G | | 8 | | 80.5 |
| R. example 3H | | 10 | | 106.5 |
| R. example 3I | | 12 | | 128.5 |
| C. example 3K | | 24 | | Uncountable |
| C. example 4J | 2.0 | 2 | Pythium myriotylum (phytopathogenic) | 0.0 |
| I. example 4F | | 4 | | 7.3 |
| I. example 4A | | 6 | | 41.3 |
| I. example 4G | | 8 | | 52.7 |
| R. example 4H | | 10 | | 69.0 |
| R. example 4I | | 12 | | 91.3 |
| C. example 4K | | 24 | | Uncountable |
| C. example 5J | 2.0 | 2 | Phytophthora nicotianae (phytopathogenic) | 0.7 |
| I. example 5F | | 4 | | 6.3 |
| I. example 5A | | 6 | | 12.7 |
| I. example 5G | | 8 | | 28.0 |
| R. example 5H | | 10 | | 68.0 |
| R. example 5I | | 12 | | 90.0 |
| C. example 5K | | 24 | | Uncountable |

TABLE 5

| C.: Comparative<br>I.: Inventive<br>R.: Reference | Film thickness (μm) | Incubation time (time) | Name of oomycete | Number of pseudohyphae which penetrated cellulose film 104 |
|---|---|---|---|---|
| C. example 2J | 2.0 | 2 | Pythium catenulatum (non-phytopathogenic) | 0.0 |
| C. example 2F | | 4 | | 0.3 |
| C. example 2A | | 6 | | 0.3 |
| C. example 2G | | 8 | | 1.0 |
| C. example 2H | | 10 | | 2.7 |
| C. example 2I | | 12 | | 4.3 |
| C. example 2K | | 24 | | Uncountable |
| C. example 6J | 2.0 | 2 | Pythium torulosum (non-phytopathogenic) | 0.0 |
| C. example 6F | | 4 | | 0.0 |
| C. example 6A | | 6 | | 0.0 |
| C. example 6G | | 8 | | 0.0 |
| C. example 6H | | 10 | | 0.3 |
| C. example 6I | | 12 | | 1.7 |
| C. example 6K | | 24 | | Uncountable |
| C. example 7J | 2.0 | 2 | Pythium inflatum (non-phytopathogenic) | 0.0 |
| C. example 7F | | 4 | | 0.0 |
| C. example 7A | | 6 | | 0.0 |
| C. example 7G | | 8 | | 0.0 |
| C. example 7H | | 10 | | 0.0 |
| C. example 7I | | 12 | | 0.3 |
| C. example 7K | | 24 | | Uncountable |

The term "uncountable" means that the penetration point of the pseudohyphae into the cellulose film 104 was not able to be observed since the pseudohyphae branched out so as to spread on the back surface 104b of the cellulose film 104.

As is clear from Table 3-Table 5, when the cellulose film 104 has a thickness of not less than 0.5 and not more than 3.7 micrometers, the phytopathogenic oomycete appears on the back surface 104b of the cellulose film 104. On the other hand, within this range of the thickness, non-phytopathogenic oomycetes seldom appear on the back surface 104b of the cellulose film 104. Therefore, the phytopathogenic oomycete 202 appears on the back surface 104b selectively in a case where the cellulose film 104 has a thickness of not less than 0.5 micrometers and not more than 3.7 micrometers. In other words, the phytopathogenic oomycete 202 appears outside of the container 100 selectively.

When the incubation time is not less than 4 hours and not more than 8 hours, the phytopathogenic oomycete appears on the back surface 104b of the cellulose film 104. On the other hand, within this range of the incubation time, non-phytopathogenic oomycetes seldom appear on the back surface 104b of the cellulose film 104. Therefore, the phytopathogenic oomycete 202 appears on the back surface 104b selectively in a case where the incubation time is not less than 4 hours and not more than 8 hours. In other words, the phytopathogenic oomycete 202 appears outside of the container 100 selectively.

Therefore, both of the following requirements (I) and (II) are required to be satisfied for the phenomenon that the phytopathogenic oomycete appears selectively on the back surface 104b.

Requirement (I): The cellulose film 104 has a thickness of not less than 0.5 micrometers and not more than 3.7 micrometers.

Requirement (II): The incubation time is not less than 4 hours and not more than 8 hours.

INDUSTRIAL APPLICABILITY

The present invention can be used to determine easily whether or not a test sample such as agricultural water or soil contains a phytopathogenic oomycete.

REFERENCE SIGNS LIST

100 First container
102 Flange
104 Cellulose film
104a Front surface
104b Back surface
170 Substrate
170a Front surface
170b Back surface
200 Test sample
202 Phytopathogenic oomycete
202a Part of Phytopathogenic oomycete
300 Second container
302 Liquid culture medium
304 Solid culture medium
402 Fluorescent agent having oomycete combining ability
500 Light source
600 Microscope

The invention claimed is:
1. A method for determining whether or not a test sample contains a phytopathogenic oomycete, the method comprising:
(a) putting the test sample on a front surface of a cellulose film;
wherein
the cellulose film has a thickness of not less than 0.5 micrometers and not more than 3.7 micrometers; and
the cellulose film comprises no through hole;
(b) leaving the test sample at rest for not less than 4 hours and not more than 8 hours after the step (a);

(c) observing a back surface of the cellulose film after the step (b); and
(d) determining that the test sample contains the phytopathogenic oomycete, if an oomycete which has penetrated the cellulose film is found on the back surface of the cellulose film in the step (c).

2. The method according to claim 1, wherein
the phytopathogenic oomycete is phytopathogenic *pythium*.

3. The method according to claim 1, wherein
the phytopathogenic oomycete is at least one selected from the group consisting of *Pythium helicoides, Pythium myriotylum, Pythium aphanidermatum*, and *Phytophthora nicotianae*.

4. The method according to claim 1, further comprising:
a step of bringing the back surface of the cellulose film into contact with a fluorescent agent having oomycete combining ability between the step (b) and the step (c).

5. The method according to claim 1, further comprising:
a step of supplying a culture medium to the test sample before the step (b).

6. The method according to claim 5, wherein
the culture medium is a liquid culture medium.

7. The method according to claim 1, wherein
the test sample is left at rest while the back surface of the cellulose film is in contact with a culture medium in the step (b).

8. The method according to claim 5, wherein
the culture medium is a solid culture medium.

9. The method according to claim 1, further comprising a substrate wherein
the cellulose film is supported by the substrate which is provided on at least one of the front surface and the back surface of the cellulose film; and
the substrate comprises a through hole having a diameter of more than five micrometers.

10. The method according to claim 9, wherein
the through hole of the substrate has a diameter of not less than eight micrometers.

11. The method according to claim 1, wherein
the test sample is solid.

12. The method according to claim 11, wherein
the solid test sample is at least one selected from the group consisting of soil and a crushed plant.

13. The method according to claim 1, wherein
the test sample is liquid.

14. The method according to claim 13, wherein
the liquid test sample is at least one selected from the group consisting of agricultural water, a liquid used for hydroponic culture, a liquid used for washing a plant, a liquid extracted from a plant, a liquid used for washing an agricultural material, and a liquid used for washing clothing or a shoe.

15. The method according to claim 1, wherein
the phytopathogenic oomycete is phytopathogenic *phytophthora*.

* * * * *